(12) United States Patent
Coppola et al.

(10) Patent No.: US 7,046,373 B2
(45) Date of Patent: May 16, 2006

(54) INTERFEROMETRIC SYSTEM FOR THE SIMULTANEOUS MEASUREMENT OF THE INDEX OF REFRACTION AND OF THE THICKNESS OF TRANSPARENT MATERIALS, AND RELATED PROCEDURE

(75) Inventors: Giuseppe Coppola, Pomigliano D'Arco (IT); Pietro Ferraro, Naples (IT); Mario Iodice, Naples (IT); Sergio De Nicola, Naples (IT)

(73) Assignee: Consiglio Nazionale Delle Ricerche, Rome (IT)

( * ) Notice: Subject to any disclaimer, the term of this patent is extended or adjusted under 35 U.S.C. 154(b) by 360 days.

(21) Appl. No.: 10/624,189

(22) Filed: Jul. 22, 2003

(65) Prior Publication Data

US 2005/0036154 A1    Feb. 17, 2005

(30) Foreign Application Priority Data

Jul. 24, 2002    (IT)    ........................ RM2002A0397

(51) Int. Cl.
*G01B 9/02*    (2006.01)
(52) U.S. Cl. .................................... 356/517
(58) Field of Classification Search ............... 356/485, 356/503, 517, 519, 520
See application file for complete search history.

(56) References Cited

U.S. PATENT DOCUMENTS

| | | | | |
|---|---|---|---|---|
| 5,034,617 A | * | 7/1991 | Isobe | 250/559.28 |
| 5,151,752 A | * | 9/1992 | Oono et al. | 356/128 |
| 5,355,218 A | * | 10/1994 | Matsuda et al. | 356/520 |
| 6,496,268 B1 | * | 12/2002 | McKie et al. | 356/503 |

* cited by examiner

*Primary Examiner*—Gregory J. Toatley, Jr.
*Assistant Examiner*—Michael A. Lyons
(74) *Attorney, Agent, or Firm*—Egbert Law Offices

(57) ABSTRACT

Interferometric system for the simultaneous measurement of the index of refraction and of the thickness of transparent materials with a single measurement operation. The system employs an interferometer as a "shear interferometer" with the advantage of varying the wavelength of the luminous source. The index of refraction and the thickness are determined in two phases. Firstly it is determined the optical path analyzing the displacement of interferometric signal obtained by orthogonal incidence; successively, by means of phase recovery techniques and the previously determined optical path value, it is possible to obtain the index of refraction of the material. From the knowledge of the index and of the optical path it is obtained the material thickness.

7 Claims, 5 Drawing Sheets

INTERFEROMETRIC SYSTEM FOR THE SIMULTANEOUS MEASUREMENT OF THE INDEX OF REFRACTION AND OF THE THICKNESS OF TRANSPARENT MATERIALS, AND RELATED PROCEDURE

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

1. Field of the Invention

The present invention refers to a system, and related procedure, for the simultaneous determination of both the index of refraction and the thickness of transparent materials, including liquids.

2. Background of the Invention

The most significant aspect of the invention is that a single measurement system is employed, based on a shear interferometric type of interferometric technique, with the further possibility of varying the wavelength of the laser source used. The evaluation of the index of refraction and of the thickness of the investigated material occurs in two steps: in the first step the variation of the "optical path" due to the variation of the wavelength of the laser source used is determined (by "optical path" is intended the product between the index of refraction and the thickness of the material analyzed); in the second step instead, the index of refraction of the material is determined, using the value of the previously identified optical path and on the basis of known phase reconstruction techniques, such as, for example, the method based on the Fourier transform. From the so calculated index of refraction and from the value of the optical path the value of the thickness of the investigated material is obtained.

The invention falls in particular, but not exclusively, in the technical field of optical characterization of materials and in the field of application of optical instrumentation manufacture. In a large number of applications, in both the scientific and industrial fields, it may be necessary to measure with an adequate accuracy, and also simultaneously, both the index of refraction and the thickness of optically transparent materials. The methods developed for the simultaneous measurement of the index of refraction and of the thickness are manifold.

However, as shown in the concerned literature, the methods currently used to measure the index of refraction and the thickness of materials require either complex measurement operations or the preliminary knowledge of the index of refraction or the thickness, or the use of costly instrumentation or of highly skilled personnel. These are all aspects that make performance of the measurement operations slow and costly.

BRIEF SUMMARY OF THE INVENTION

The invention which is the object of this patent application, represents a significant improvement with respect to other systems of measurement of the index of refraction and of thickness. In fact, scope of the inventors is to develop a system able to determine simultaneously both the index of refraction and the thickness of transparent materials by means of "a single measurement operation", providing a high measurement precision. The submitted invention is thus a measurement system where a "shear interferometric" type of interferometry is employed, with the additional advantage of varying the wavelength of the luminous radiation. The system, at present preferred by the inventors for performing the measurement, is described hereinafter in its essential elements:

- provide a holder that serves to house the material whose index of refraction and thickness are to be measured;
- said holder is placed on a precision rotating stage and then duly inserted in the measurement system so that a coherent and monochromatic light beam, is transmitted through the sample to be measured;
- the coherent light going through the sample is subject to various reflections and refractions at the sample interfaces, thereby producing an interference signal;
- from observation of the phase variation of the interference signal, obtained by tuning of the wavelength of the coherent light, the optical path is obtained;
- from said optical path, and observing the interference signal, obtained for each fixed wavelength of the coherent light source, the index of refraction of the material is obtained;
- from said index of refraction value and from the optical path value the thickness of the sample to be measured is obtained.

The emitted wavelength of the coherent and monochromatic light source must be easily tuned and controlled.

With the submitted invention only one measurement operation will be required, since for each fixed angular position, i.e. for each fixed value of the optical path, the variation of the interferometric signal will depend only on the variation of the wavelength of the coherent source; whereas for each fixed wavelength, by varying the angular position of the sample, parts of the coherent light within the sample are differently and laterally sheared, generating an interferometric signal which is a function of the angle of incidence. Said lateral shear depends exclusively on the presence of the material to be characterized, for each angle of incidence.

According to the authors the best way to realize this invention is to use a system where the sample is in rotation with respect to a coherent and monochromatic light beam, which emitted wavelength can be tuned. Said system has particular simplicity of use, versatility and compactness characteristics. The system can have configurations different from those described in the present invention and can be developed with a different number and type of optical components without prejudicing or changing the system forming the object of the present invention.

The invention is now being described on the basis of a version at present preferred by the inventors and with reference to the attached drawings.

BRIEF DESCRIPTION OF THE VIEW OF THE DRAWING

DETAILED DESCRIPTION OF THE INVENTION

Figure 1:
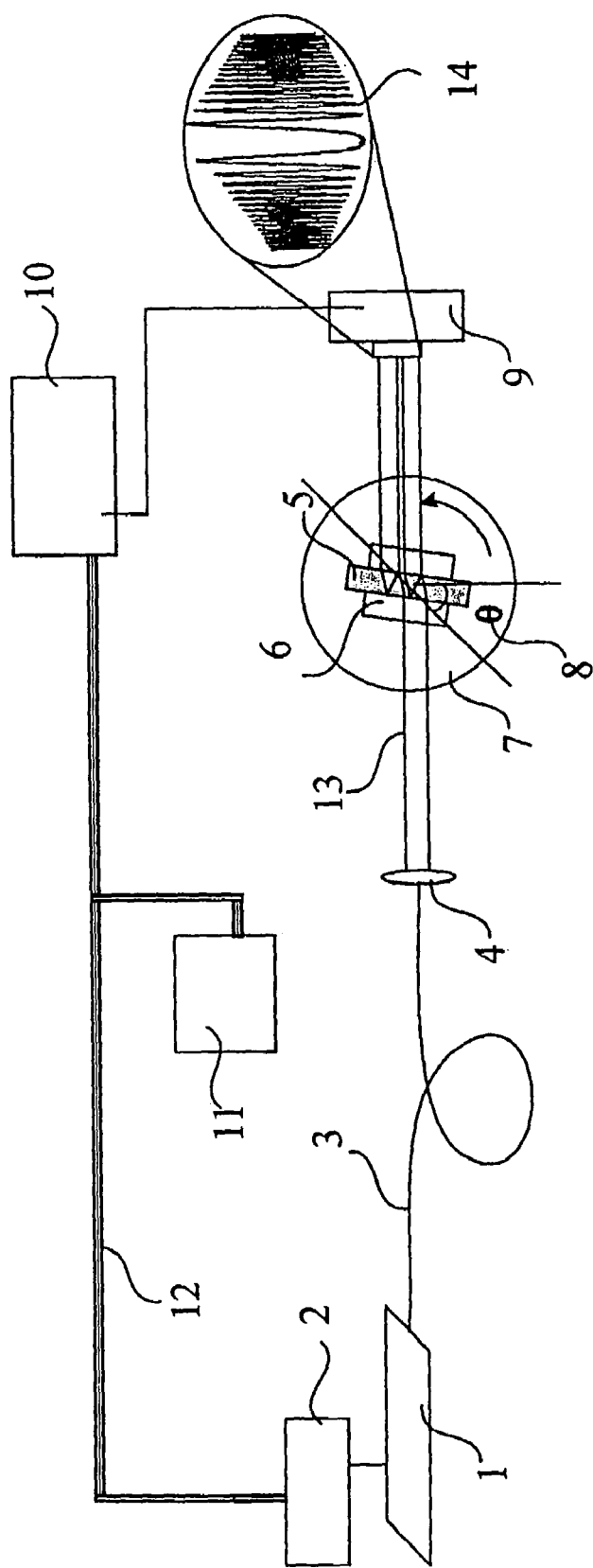
FIG. 1 is a schematic view of the system for the simultaneous measurement of the index of refraction and the thickness of transparent materials.

With reference to FIG. 1, the optical components for developing the measurement system, the position of the cell, rotating base 7 and the system of analysis of interferometric signals 10, 11, 12 are shown. To be more precise, below are listed all the parts comprising the system:

- 1 laser diode
- 2 laser diode supply
- 3 optical fiber
- 4 collimator
- 5 sample to be measured
- 6 sample holder
- 7 precision rotating stage
- 8 angle of incidence
- 9 photodiode
- 10 oscilloscope
- 11 personal computer
- 12 Bus IEEE-488

Observing FIG. 1, it can be seen that the system composed of a laser diode DFB 1, the laser beam, in output an optical fiber 3, is collimated through collimator 4. Along the direction of propagation of laser beam 13 is placed the sample to be measured 5. Laser radiation 13, after traversing sample 5, impinges upon photodiode 9. Through oscilloscope 10 it is possible to acquire the interferometric signal on a personal computer 11 for subsequent analyses. The sample is placed on a precision rotating stage 7. By means of personal computer 11, bus IEEE-488 12 and supply 2 it is possible to control the wavelength of the laser radiation emitted by source 1. Once the wavelength of laser source 1 is fixed, if the sample to be measured 5 is caused to rotate by means of rotating base 7, there is a variation of optical path between the rays that propagate inside sample 5. In the case where the index of refraction n of the traversed material is constant, the optical path is expressed as the product of geometric path d by index of refraction n. The optical path variation depends on angle of incidence 8 and this produces interferometric signal 14. Through personal computer 11, bus IEEE-488 12 and supply 2, it is possible to vary the wavelength of laser source 1 and then, for each fixed angle of incidence 8, to vary the phase of interferometric signal 14.

Figure 2:
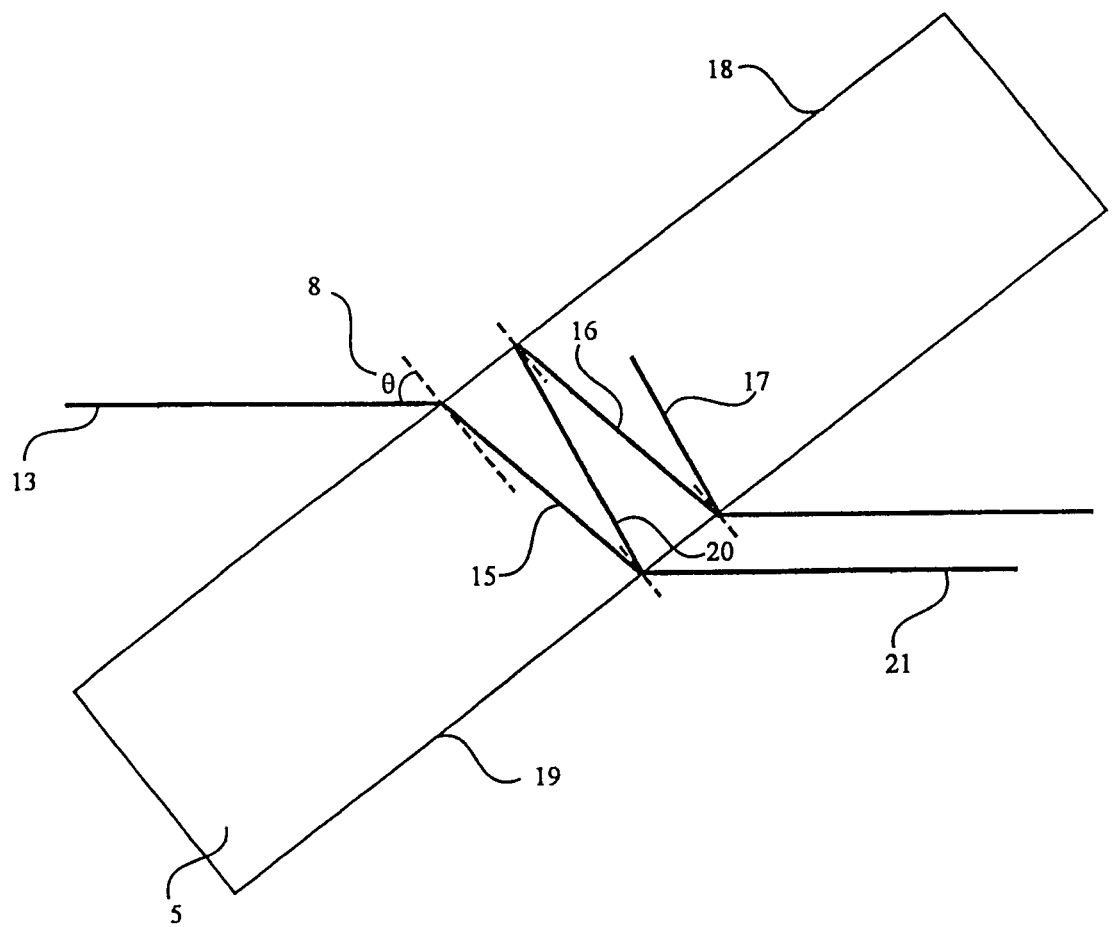
FIG. 2 is a schematic view of the sample of material to be used with the relevant variations of direction of the incident radiation.

With reference to FIG. 2, which shows a view from above of the sample to be measured, it is noted that in the case where the sample is of constant thickness and uniform index of refraction, then the difference of optical path, between the various rays 15, 20, 16, 17 which propagate inside the sample, is due only to the reflections and refractions undergone by said rays on surfaces 18 and 19 of the sample. The optical path difference depends on angle of incidence 8 and on said difference will depend the acquired interferometric signal. In particular ray 13 is subject to a refraction at air-sample surface 18, propagates within the sample (ray 15) and part of it is subject to a refraction at sample-air interface 19 (ray 21) and part is reflected by sample-air interface surface 19 (ray 20). This part, after being subjected to a further reflection on interface 18 and a refraction at surface 19, will exit from the sample. Obviously part of ray 16 will be reflected by surface 19 generating ray 17, which will undergo the same experience as ray 20. If the sample is constituted by homogeneous material, with uniform thickness and parallel walls, it is easy to demonstrate that the interferometric signal can be determined by the following equation:

$$I(\theta) = I_0 + \gamma \cos\left(\frac{4\pi n d}{\lambda}\sqrt{1 - \frac{\sin^2\theta}{n^2}}\right) \quad (1)$$

where $\lambda$ is the wavelength of the laser used; $I_0$ is linked to the intensity of the interfering beams, and $\gamma$ depends on the coherence of the luminous source.

Figure 3:
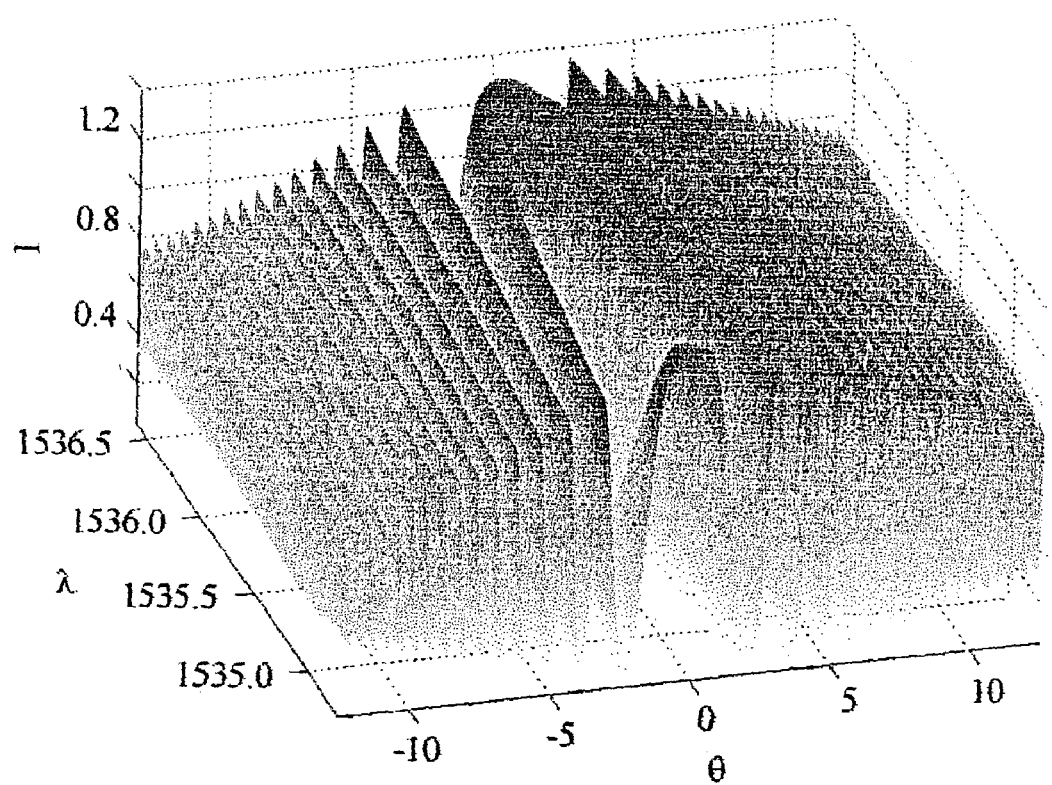
FIG. 3 is a diagrammatic illustration showing graphically the interferometric signal obtained upon varying of the angle of incidence and for each wavelength of the coherent tuneable light source.

With reference to FIG. 3, the typical interferometric signal is shown, for a silicon sample, obtained upon varying of the angle of incidence $\theta$, for each wavelength $\lambda$. From the symmetry of the figure the position of normal incidence ($\theta=0°$) can easily be determined. In such position, observing the phase variation of the interferometric signal upon varying of the wavelength, it is possible to determine the optical path within the sample to be measured.

Figure 4:
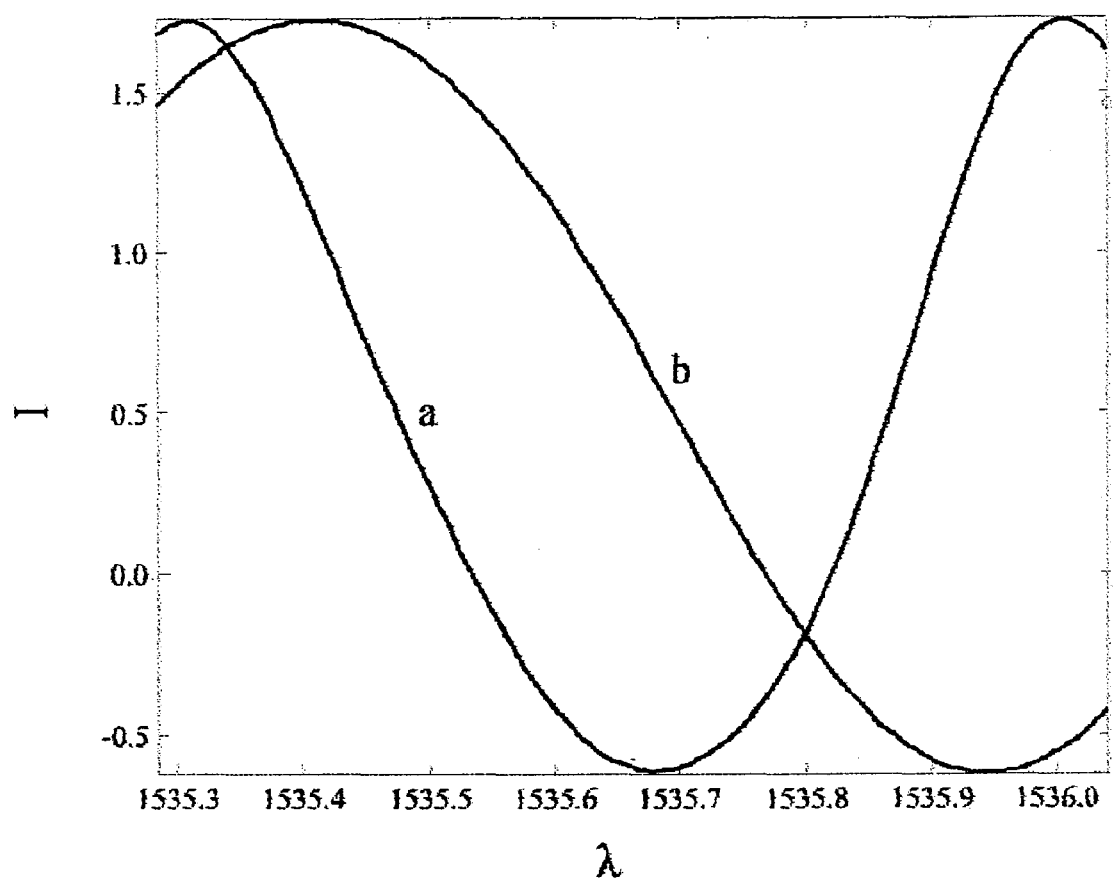
FIG. 4 is a diagrammatic illustration showing graphically the phase variation of the incident radiation according to the wavelength of the coherent light source relative to the measurement of the optical path of the silicon (case a) and of the Lithium Niobate (case b). In both cases the incidence is orthogonal to the sample.

In FIG. 4 is shown, as example, the variation of the interferometric signal obtained by normal incidence ($\theta=0°$) upon varying of the wavelength of the coherent light source. Said signal can be described by the following equation:

$$I_{\theta=0}(\lambda) \approx A + \sum_{m=1}^{3} B_m \cos\left[m\frac{4\pi d}{\lambda} + \Delta\phi\right] \quad (2)$$

From the analysis of said signal and by interpolating the experimental data it is possible to obtain the optical path n·d. Case (a) refers to a silicon sample, while case (b) refers to a lithium niobate sample.

Figure 5:
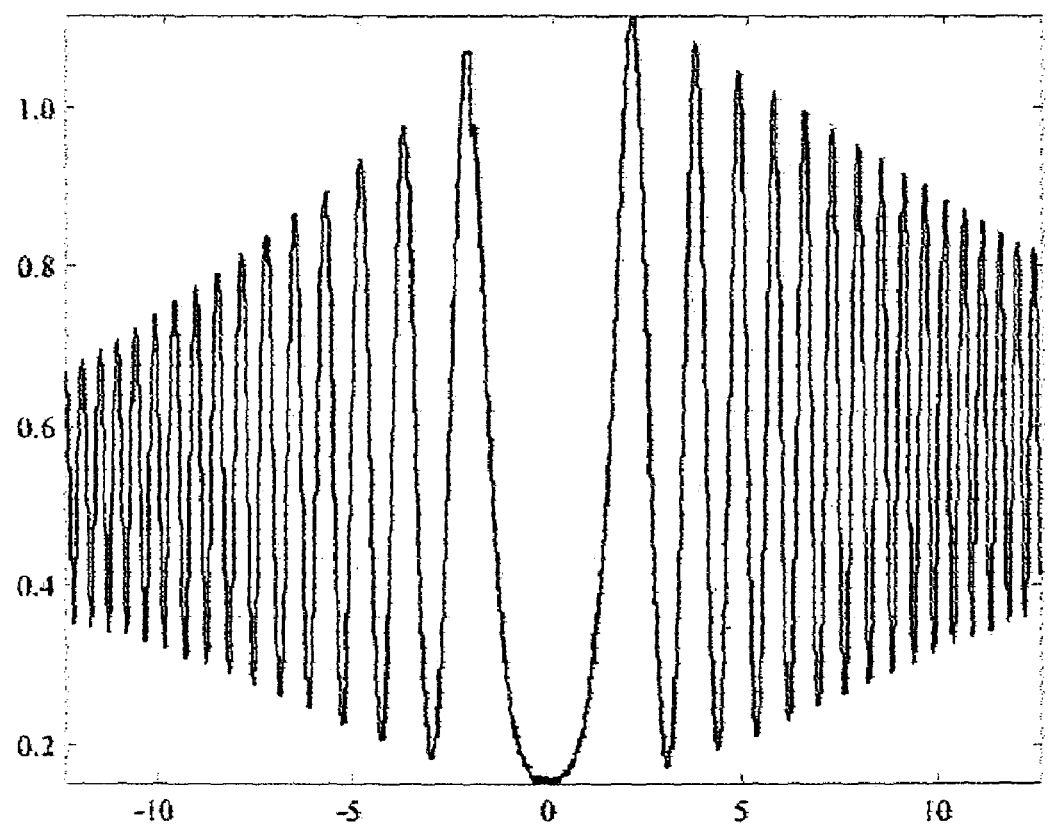
FIG. 5 is a diagrammatic illustration showing a typical interferometric signal for a fixed wavelength and upon varying of the angle of rotation of the sample.

In FIG. 5 is shown instead, the interferometric signal according to the angle of incidence and for a fixed wavelength. The signal is thus described by equation 1, with $\lambda$ fixed. Using the previously determined optical path value, it is possible to obtain the index of refraction of the analyzed sample by means of well known phase retrieval techniques. From the simultaneous knowledge of the optical path and of the index of refraction it is consequently possible to determine the value of the sample thickness.

In conclusion, the invented system offers the possibility of determining from the same family of acquired interferometric signals both the index of refraction and the thickness by means of two distinct phases, so as to improve the accuracy with which the two entities are determined.

Should it be desired to measure the index of refraction and the thickness of transparent materials with the methods known prior to the present invention, it is necessary to use either two separate measurement systems or complex measurement operations or systems with instrumentation which is complex, costly and usable only by highly skilled personnel. Furthermore, with the submitted system it is also possible to determine the index of refraction of liquid substances; in fact, it suffices to build a small cell of homogeneous material with uniform thickness and parallel walls. Said cell will contain the liquid material to be characterized and will be placed above rotating stage 7 shown in FIG. 1.

We claim:

1. A system for measuring an index of refraction and a thickness of a transparent material, the system comprising:
    a laser source suitable for producing an emission;
    a power supply connected to said laser source;
    a collimator cooperative with said laser source so as to collimate the emission of said laser source;
    a sample of the transparent material;
    a rotating stage supporting said sample thereon at a select angle with respect to the collimated emission of said laser source;
    a photodiode means positioned on an opposite side of said rotating stage from said laser source, said photodiode means for receiving the collimated emission as passed through said sample;
    a oscilloscope means connected to said photodiode means, said oscilloscope means for producing an interferometric signal from the collimated emission received by said photodetector means;
    a control bus electrically connecting said oscilloscope means to said power supply; and
    a computing means connected to said control bus, said computing means for varying a wavelength of the emission of said laser source through said power supply, said computing means for determining a measurement of an optical path of the collimated emission of said sample so as to determine a thickness of said sample, said computing means being a personal computer.

2. The system claim 1, said sample being of a homogeneous material having a planar and parallel faces.

3. The system of claim 1, said sample positioned vertically on said rotating stage, said sample having a surface facing said laser source.

4. The system of claim 1, said emission of said laser source passing through said sample so as to produce reflections and refractions within said sample, said interferometric signal corresponding to the reflections and refractions.

5. The system of claim 1, said computing means for measuring the optical path by evaluating said interferometric signal obtained by varying an angle of incidence for a respective varied wavelength of the emission from said laser source.

6. The system of claim 5, said computing means for determining the index of refraction by analyzing the interferometric signal relative to the angle of incidence for a particular wavelength of the emission of said laser source.

7. A method of measuring an index of refraction and a thickness of transparent material comprising:
    providing a support that houses the transparent material;
    placing said support on a rotating stage;
    traversing a coherent and monochromatic light beam through the transparent material so as to cause various reflections at interfaces within the transparent material so as to create an interference signal;
    obtaining an optical path from an observation of a phase variation of the interference signal following a variation of the wavelength of the coherent and monochromatic light beam;
    obtaining the index of refraction from the optical path and the observation of the interference signal obtained for each fixed wavelength of the coherent and monochromatic light beam; and
    determining the thickness of the transparent material from the index of refraction and the optical path.

* * * * *